(12) United States Patent
Matheis et al.

(10) Patent No.: US 11,044,984 B2
(45) Date of Patent: Jun. 29, 2021

(54) CARRYING DEVICE FOR A GAS EXCHANGE DEVICE

(71) Applicant: Novalung GmbH, Heilbronn (DE)

(72) Inventors: Georg Matheis, Heilbronn (DE); Esther Novosel, Stuttgart (DE); Reinhold Beuter, Rangendingen (DE); Jörg Schneider, Starnberg (DE); Josef Bogenschütz, Bisingen (DE)

(73) Assignee: NOVALUNG GMBH, Heilbronn (DE)

( * ) Notice: Subject to any disclaimer, the term of this patent is extended or adjusted under 35 U.S.C. 154(b) by 163 days.

(21) Appl. No.: 15/738,943

(22) PCT Filed: May 9, 2016

(86) PCT No.: PCT/EP2016/000751
§ 371 (c)(1),
(2) Date: Dec. 21, 2017

(87) PCT Pub. No.: WO2017/001034
PCT Pub. Date: Jan. 5, 2017

(65) Prior Publication Data
US 2018/0177283 A1 Jun. 28, 2018

(30) Foreign Application Priority Data

Jun. 29, 2015 (EP) ..................................... 15001921

(51) Int. Cl.
*A45F 3/14* (2006.01)
*A61M 1/16* (2006.01)
*A61M 1/14* (2006.01)
*A45F 3/16* (2006.01)

(52) U.S. Cl.
CPC ................. *A45F 3/14* (2013.01); *A61M 1/14* (2013.01); *A61M 1/1698* (2013.01); *A45F 2003/142* (2013.01); *A45F 2003/144* (2013.01); *A45F 2003/166* (2013.01); *A61M 2209/088* (2013.01)

(58) Field of Classification Search
CPC .......... A45F 2003/144; A45F 2003/166; A45F 2003/142; A45F 3/14; A61M 2209/088; A61M 1/14; A61M 1/1698
USPC ....................................................... 224/576
See application file for complete search history.

(56) References Cited

U.S. PATENT DOCUMENTS

| 4,739,913 A | 4/1988 | Moore |
| 5,250,027 A | 10/1993 | Lewis et al. |
| 5,263,925 A | 11/1993 | Gilmore, Jr. et al. |

(Continued)

FOREIGN PATENT DOCUMENTS

| CA | 2797702 A1 | 11/2011 |
| DE | 102009050406 A1 | 5/2011 |

(Continued)

*Primary Examiner* — Nathan J Newhouse
*Assistant Examiner* — Matthew T Theis
(74) *Attorney, Agent, or Firm* — Dinsmore & Shohl LLP

(57) ABSTRACT

A carrying device for a portable gas exchange device has at least one first holding strap which is designed to be worn around a torso of a patient, thereby allowing the carrying device to be supported on the patient. The carrying device further includes a fastener which is designed to fasten a portable gas exchange device. Also provided is a carrying system which consists of a carrying device and a gas exchange device.

19 Claims, 9 Drawing Sheets

(56) References Cited

U.S. PATENT DOCUMENTS

| | | | | |
|---|---|---|---|---|
| 5,928,189 | A * | 7/1999 | Phillips | A61M 16/0677 604/65 |
| 6,547,851 | B2 * | 4/2003 | Warren | B01D 53/047 95/130 |
| 6,651,659 | B2 * | 11/2003 | Izuchukwu | F17C 1/02 128/205.15 |
| 7,418,741 | B2 * | 9/2008 | Rogers | A41D 13/1236 2/114 |
| 7,718,144 | B2 | 5/2010 | Monzyk et al. | |
| 8,906,300 | B2 * | 12/2014 | Wang | A61M 1/26 422/46 |
| 2005/0072426 | A1 * | 4/2005 | Deane | A61M 16/10 128/204.26 |
| 2005/0085761 | A1 | 4/2005 | Wang et al. | |
| 2008/0014115 | A1 | 1/2008 | Johns | |
| 2009/0120864 | A1 | 5/2009 | Fulkerson et al. | |
| 2010/0122995 | A1 * | 5/2010 | Thomas | A45C 11/00 224/681 |
| 2010/0308086 | A1 * | 12/2010 | Chapuis | A45F 3/04 224/148.2 |
| 2012/0138058 | A1 | 6/2012 | Fu et al. | |
| 2012/0209228 | A1 | 8/2012 | Croizat et al. | |
| 2013/0296633 | A1 | 11/2013 | Strueber | |
| 2014/0276498 | A1 | 9/2014 | Connor et al. | |
| 2016/0296685 | A1 * | 10/2016 | Wu | A61M 1/1629 |

FOREIGN PATENT DOCUMENTS

| | | | | |
|---|---|---|---|---|
| EP | 3277338 A1 | 2/2018 | | |
| JP | S55123510 U | 9/1980 | | |
| WO | WO-0129421 A1 * | 4/2001 | | A45F 3/14 |
| WO | WO-2014/085620 A1 | 6/2014 | | |
| WO | 2015100288 A1 | 7/2015 | | |

* cited by examiner

CARRYING DEVICE FOR A GAS EXCHANGE DEVICE

CROSS-REFERENCE TO RELATED APPLICATIONS

This application is the U.S. national stage of PCT/EP2016/000751 filed May 9, 2016, which claims priority of European Patent Application 15001921.4 filed Jun. 29, 2015 of which is hereby incorporated by reference in its entirety.

FIELD OF THE INVENTION

The invention relates to carrying device, as well as a carrying system.

BACKGROUND OF THE INVENTION

Gas exchange devices are known that are gas supply or gas removal devices in which one or more gases may pass from one medium into another medium, or devices which enable the exchange of one or more gases between two media. Such devices are used in chemistry, biotechnology, and medicine. An important intended use in medicine is the enrichment of a biological liquid—in particular, blood—with oxygen, and/or the removal (thus depletion) of carbon dioxide from the liquid—especially, blood. Such measures are necessary when treating various pulmonary diseases, for example. Furthermore, such measures may also be necessary in case of acute respiratory failure, for example, as well as for the replacement of a lung; while bypassing a lung with an extracorporeal circulatory system; to a different extent, in case of mechanical cardiac support; and to enable operating on stopped hearts.

Currently, the only long-term, effective therapeutic option for patients with terminal functional lung disease is to perform a lung transplant. There is no other medical solution for permanently replacing the function of the lungs. For patients who suffer from chronic pulmonary diseases such as COPD and AECOPD and are not being considered or not immediately being considered for a lung transplant, there is therefore a need for artificial lung support or lung replacement methods.

In order to make possible such a lung support or lung replacement method, what are known as blood gas exchangers are known from the prior art.

A blood gas exchanger, also designated as an oxygenator or artificial lung, is used either for complete, temporary takeover of the lung function during an open heart operation, or as a complete or partial long-term support of the lungs in the intensive care unit. The primary function of a blood gas exchanger consists in delivery of oxygen to the blood (oxygenation) and in the take-up of carbon dioxide from the blood (decarboxylation).

In addition to application in oxygenation and decarboxylation, in some therapy uses, it is already sufficient to perform only a decarboxylation. This is thereby what is known as an extracorporeal reduction of $CO_2$ ($ECCO_2R$). For this, blood is continuously removed via a venous access of the patient, pumped extracorporeally through a blood gas exchanger, cleaned there of $CO_2$, and venously supplied again to the patient.

For gas exchange in such blood gas exchangers, oxygen is typically used, which is available in any hospital, either directly via a wall connection or via oxygen bottles. The oxygen is then supplied via a controllable gas diaphragm to the blood gas exchanger.

Pumping systems for $ECCO_2R$ applications are, in principle, operated on a stationary power grid. In the event of an emergency, e.g., a power failure, an emergency power supply may be maintained by means of battery operation. Since medical facilities normally possess emergency power generators, however, a battery operation is time-limited and, with the known gas exchange devices, is normally not designed for long-term operation or mobile operation. A known blood gas exchange system which does possess a mobile power supply, however, necessitates carrying along a rollable carrier device to carry the plurality of different, sometimes cumbersome, components of the blood gas exchanger, and, in particular, gas canisters.

Due to its size, weight, and the arrangement of connections such as for blood-carrying tubes, the use of the known gas exchange devices has therefore essentially been limited until now to stationary applications in which the patient, conscious or sedated, is lying in bed. Patients with chronic pulmonary diseases that are reliant on these known gas exchange devices are thus severely limited in their mobility. This does not just significantly reduce the quality of life of the patients; modern therapy approaches that stress a mobilization of the patient cannot be implemented.

Gas exchange devices that are suitable in principle for mobile use are the subject matter of recent developments. To ensure mobility for a patient who relies on such a gas exchange device, it is desirable for the gas exchange device to be safely transportable. When conventional carrier devices—similar to a rollable infusion stand, for example—are used, there is always the danger that the carrying device will become unforeseeably separated from the patient—for example, when the patient falls, or individuals or objects come between the patient and the carrying system. In the worst case, this can cause an extracorporal blood circulatory system to be interrupted or even destroyed. This can be associated with serious health consequences for the patient, up to and including blood loss, oxygen deficiency, or carbon dioxide poisoning, with severe consequences.

Known gas exchange devices for supporting lung function thus have the same disadvantages as are also familiar from lung replacement devices. In this case as well, a gas canister must also be transported, and different devices must be worn distributed over the body or transported separately.

SUMMARY OF THE INVENTION

The underlying aim of the present invention is to prevent at lease one of the disadvantages of the prior art and enable a transportable gas exchange device to be safely transported. An additional aim is to enable a patient to transport a gas exchange device over an even longer period of time—preferably, directly on the patient's body. In particular, transportation of a gas exchange device is to be enabled that is designed for mobile, portable use on the patient's body, e.g., by a particularly compact design, for use as a lung support system.

This aim is achieved by a carrying device according to claim 1, as well as a carrying system according to claim 10. Advantageous embodiments of the invention are the subject matter of the dependent claims.

A first aspect of the present invention relates to a carrying device for a portable gas exchange device—in particular, a portable gas exchange device as a life-support system in the form of a gas exchange. The carrying device has at least one first carrying strap which is designed to go around a patient's torso and thereby allow the carrying device to be supported on the patient. Moreover, the carrying device has at least one fastening means that is designed to fasten a portable gas exchange device to the carrying device. A gas exchange device can accordingly be safely and comfortably worn by a patient. The term "gas exchange device" within the meaning of the present invention includes, in particular, such devices as enable a gas supply with one or more pre-designated gases, such as in the form of a supply air component. If the device according to the invention is used, in particular, only for supporting, and not for completely replacing, lung function, it can become unnecessary to carry additional gas canisters—in particular, for supplying oxygen. The carrying device according to the invention can thereby enable a gas exchange device—preferably, with all of the components needed for lung support—to be worn directly on a patient's body. This can significantly increase patient mobility.

In addition, at least one second carrying strap can be provided that is designed to go over at least a first shoulder of a patient. In this manner, the weight of a carrying device and components attached thereto can be deflected.

In the context of the present invention, "belts" designate sections of the carrying device that are designed as separate units independent of each other. Alternatively, the belts can also be formed as a single part with each other and/or with a subsequent carrying structure.

By providing at least two belts—a belt that can go around a patient's torso and a belt that can go around at least one shoulder—secure attachment of the carrying device on a patient's body can be enabled. For example, the second carrying strap can be designed such that it can go diagonally across the torso and a first shoulder of a patient. The first carrying strap can be designed so that it can run in a substantially horizontal direction, e.g., around a patient's waist, so that a fastening of the carrying device can be executed in a manner similar to a three-point belt system. In this context, the second carrying strap, in particular, can also be connected to the first carrying strap, or at least run sectionally around the first carrying strap.

A mobile or portable gas exchange device can be fastened to the carrying strap by the fastening means. In this manner, a portable gas exchange device can be securely worn by a patient directly on the patient's body. This can increase patient mobility and thereby promote a patient's recovery or therapy. Moreover, a danger of damaging the portable gas exchange device or an extracorporal blood circulatory system can be reduced. The fastening means for fastening the gas exchange device can be designed in a front region of the first carrying strap. The fastening means can be designed as single part with one of the carrying straps—preferably, the first carrying strap—or fastened as a separate element on one of the carrying straps.

According to one of the embodiments of the present invention, at least the first and/or the second carrying strap can have a means for adapting the length, for example, of the first and/or second carrying strap. In this manner, the carrying device can be adapted to the individual physique of the patient. This can increase wearing comfort. Adapting the length of a belt, such as the second carrying strap, can, for example, be enabled, in that the belt has two legs or belt sections that are each provided with a locking means section, wherein the locking means sections are complementary to each other and can establish a connection with each other—in particular, a reversibly openable and closable connection. The locking means sections can be arranged in any or in predetermined positions relative to each other.

In a similar manner, the first carrying strap can also be designed to have a changeable length through the use of a locking means on an open end section of the carrying strap. In this manner, an adjustment in the length of the first carrying strap can be more easily adapted to a circumference of the patient's body. This can increase wearing comfort.

The carrying device can, moreover, have a third carrying strap. The third carrying strap can, in particular, be designed to be identical and/or symmetrical to the second carrying strap and configured to go around a second shoulder of a patient. This can improve a distribution of force for wearing a portable gas exchange device in that an even load on both shoulders of the patient can be enabled. This can also reduce undesired slippage of the carrying device. Of course, the third carrying strap can also have means for adapting its length.

The carrying device according to the invention can at least have a closing means for opening and closing at least one of the carrying straps. The closing means for opening and closing the carrying device can also coincide with the means for adjusting a length of a carrying strap. In particular, a closing means for opening and closing the first carrying strap can be provided. In this manner, the carrying device can be more easily placed on a patient's body. This can be particularly advantageous when the patient is already connected to an extracorporal blood circulatory system with a portable gas exchange device, so that the carrying device can be put on without impairing the extracorporal blood circulatory system.

The at least one closing means can be designed as an adherence fastener, and/or a clamping fastener, and/or an engaging fastener, or one of the listed closing means. In particular, it is also possible that the closing means is designed over an entire area, i.e., it has a plurality of closing elements that have over a certain area, such as a width of the carrying strap provided with the closing means. Adherence fasteners are understood to be those types of closing means that are based upon an adherence principle of two elements, such as the adherence of one or more magnet pairs, or the accumulated adhesive effect in a hook-and-loop (Velcro®) fastener. Clamping fasteners refers to fasteners that are based upon clamping two components onto each other or in(to) each other, such as is the case, for example, with pushbuttons or buckle fasteners. Engaging fasteners refers to fasteners that are based upon a principle of engagement, such as hooking two hooks and/or eyelets. It is understood that also combinations of such closing means are conceivable, which, for example, complement each other or are provided cumulatively independently of each other, for example, as a safety measure. Any type of belt closure is also included under the aforementioned types of closing means within the context of the invention. Of course, other types of closing means are possible which are suitable for fastening a carrying strap to itself, to another carrying strap, or to a section of the carrying device.

The carrying device according to the invention can be designed so that the at least one closing means connects, for example, the second or the third carrying strap to the first carrying strap when in a closed state. In particular, two of the carrying straps can also be designed as a single part together, such as the second carrying strap and a third carrying strap. Moreover, all carrying straps can be designed as a single part together. In this manner, the supporting device can, for example, be designed like a vest, with two shoulder carrying straps that are connected to each other along a vertical section on a front and/or rear side. This can, for example, simplify the handling of the carrying device for a patient and can reduce the number of closing means.

According to additional embodiments, the carrying device can moreover have a cable holder. The cable holder can, in particular, be provided on the first carrying strap and is designed to hold and/or secure a cable—in particular, on the first carrying strap. This can make it possible to design the carrying device for a portable gas exchange device to be safer for a patient, since cables that can be provided on a gas exchange device can be safely held on the patient's body. The cable holder can be a self-closing holder, such as a holder that closes under spring force. The cable holder can be dimensioned so that a cable is run loosely by the cable holder or can be clamped in the cable holder. By clamping a cable, unintentional tension on the cable can be deflected by the cable holder without the cable moving or being displaced in the cable holder. In the event that a supply cable for the gas exchange device is held in the cable holder, unintentionally pulling out the cable from the gas exchange device or damage to components connected to the cable can thereby be prevented, or at least reduced.

In alternative embodiments, the cable holder can also run within a carrying strap—in particular, within the first carrying strap. "Within" is intended to be a side of the carrying strap facing the patient's body when the carrying device is in a state of being placed on a patient's body. Of course, the cable holder can also have a longitudinal extension such that the cable holder extends along the carrying strap—in particular, the first carrying strap. The cable holder can therefore also form a tunnel section, running inside or outside of the carrying strap, in which a cable can be held and guided.

In this manner, safe running of the cable can be ensured, so that a negative impact on the patient can be reduced.

Furthermore, in some embodiments of the present invention, it is conceivable that the carrying device has a hose holder for holding one or more hoses. The hose holder can, in particular, be designed to hold a hose of an extracorporal blood circulatory system. The hose holder can, in particular, be designed so that the hose(s) held therein are run on the inside of the carrying device, i.e., on a side facing a patient's body. Heat loss of a fluid—in particular, blood—conducted in the hose(s) can thereby be reduced.

Preferably, the first carrying strap of the carrying device is curved radially to the outside at least when the closing means is in a closed state, wherein the radius of curvature differs in sections. The first carrying strap is thereby optimally adapted to a position on a patient's waist.

A second part of the present invention relates to a carrying system that has a carrying device—in particular, according to the first part of the present invention—as well as a portable gas exchange device. The gas exchange device has a fastening means which is complementary to a fastening means of the carrying device, so that the gas exchange device can be fastened to the carrying device—in particular, reversibly. Such a carrying system can allow a patient to move in a mobile manner, at least within a limited radius and independently of stationary systems.

The gas exchange device of the carrying system can have a control unit. The control unit can in turn have a fastening means that is designed to be fastened to the carrying device—in particular, to one of the belts, such as the first carrying strap of the carrying device—and/or to the gas exchange device. In this manner, the control unit can be securely mounted directly adjacent to the gas exchange device and can enable a patient or assistant to quickly access the control unit and the functions of the gas exchange device.

In some embodiments of the present invention, the control unit can also be designed to be directly integrated in the gas exchange device.

The gas exchange device can moreover have at least one cable for connecting to the control unit, wherein the cable can be held in a cable holder formed on the carrying device. This can make it possible to safely stow the cable and thus reduce a negative impact on patient. Of course, the control unit and the portable gas exchange device can, alternatively, also be connected to each other wirelessly. For example, a radio link, Bluetooth link, infrared link, or other types of wireless transmission and transmission protocols can be used to connect the control unit to the gas exchange device. This can circumvent the use of the cable and thereby reduce the weight of the carrying system and increase the wearing comfort of the carrying system.

The cable holder of the carrying system can in principle be designed as described above with regard to the carrying system device—in particular, also as an elongated holder for running a cable of a predetermined length along a patient's body.

Furthermore, at the control unit, a means may be provided that allows an attachment of the control unit to the portable gas exchange device and/or the carrying device. For this, at the gas exchange device and/or the carrying device, a complementary means may be provided so that, for example, an attachment section of the control unit engages with an attachment section of the gas exchange device, and may enable a reliable attachment of the gas exchange device. In some embodiments, a flap can be provided on one of the carrying straps—in particular, on the first carrying strap—which flap is designed and dimensioned to receive the attachment section of the control unit.

The attachment of the control unit may, for example, be provided at the housing of the gas exchange device. Alternatively, an attachment of the control unit to a carrier system of the gas exchange device may also be provided. In addition to this, an attachment of the control unit directly to the clothing of a patient may also take place. In addition to this, the attachment means of the control unit may also be provided for attaching the control unit to a support structure, e.g., to a patient bed, or to a carrier system for medical devices in a hospital room.

In particular, the attachment means of the control unit may have a hook-shaped form that enables a hooking of the attachment means to a complementary receptacle section, or, for example, to a tube-shaped element or an outer contour of the housing of the gas exchange device. In addition to this, an attachment to a flat structure—for example, to a rolling chair back or the like—is conceivable. For this, the attachment means of the control unit may, for example, be designed with a spring arm under a spring pre-load, so that a clamping due to the spring pre-load of the attachment means provides a sufficient retention force for attaching the control unit. Moreover, the attachment means or an additional stand means may be designed and formed at the control unit such that said control unit may be set up on a support—for example, a table or a roll container or the like.

It is, moreover, conceivable for the carrying device of the carrying system to be designed with an integrated cable that is designed to connect the control unit to the gas exchange device. In this case, the carrying device can—for example, on a carrying strap—be provided with corresponding connections. A connection can, for example, also be designed to be integral with a fastening means for fastening the gas exchange device to the carrying device or a fastening means for fastening the control unit to the carrying device or the gas exchange device. An "integral" design is also to comprise the embodiments of the invention in which a fastening means and a connection—in particular, an electrical connection—for connecting to the control unit are made that are separate locally, but coupled to each other. This concerns, in particular, those instances in which, by fastening the gas exchange device to the carrying device, there is also an indirect—in particular, electrical—connection to the carrying device and/or control unit.

The gas exchange device, which, in particular, can be a device for lung support, essentially consists of a housing, a pump system, and a gas exchange means. The gas exchange means is preferably held, together with the pump system, in the housing of the gas exchange device. This makes it possible to provide a compact gas exchange device that can easily be worn on the body, which a patient or assistant can easily, safely, and reliably attach close to or directly on a patient's body. This can increase freedom of movement and wearing comfort for a patient. Moreover, such a gas exchange device can increase safety for a patient, since the compact and integrated design of the gas exchange device can reduce external access to the gas exchange device.

Moreover, it is conceivable within the context of the invention that the control unit is designed to be at least partially integrated in the carrying device. Accordingly, a display unit, for example, can be designed to display relevant parameters of the gas exchange device at or on the caring device. It is also conceivable for the carrying device, the gas exchange device, and/or the control unit to have an alarm button and/or a mobile communications device—in particular, for establishing a manual or automatic emergency call connection in the event of a malfunction of the gas exchange device.

Moreover, it should be noted that the different embodiments of the present invention relate, in particular, to a device for lung support, i.e., a device that only partially fulfills a lung's function. Especially since the lung's function is supported, for example, by reducing the $CO_2$ concentration in blood, but is not, however, entirely replaced, a portable, compact, and highly mobile gas exchange device can be provided, since heavy gas canisters, such as oxygen canisters, do not have to transported as well.

Correspondingly, some embodiments of the carrying system according to the invention have an ambient air suction section. The ambient air suction section can, in particular, be provided on the gas exchange device of the carrying system. This ambient air suction section can have one or more filters for filtering the ambient air. The aspirated ambient air can then be conducted to a gas exchange section of the gas exchange device—for example, by means of a hose system. Particularly when used for lung support by reducing $CO_2$ in the blood, it is sufficient to use ambient air, i.e., normal respiratory air, which has a $CO_2$ content of generally less than 0.05%, for depleting $CO_2$ in the blood. $CO_2$ can be reduced independently of blood oxygenation, as can be the case, for example, in the event of COPD. Carrying oxygen canisters or other gas canisters, and the associated transportation of heavy pressure tanks, is, therefore, not absolutely necessary. This makes it possible for a physically impaired patient to independently carry the carrying system according to the invention, which is not possible when heavy pressure tanks are carried along.

Preferred embodiments of the invention therefore relate to a carrying system that has no external gas compression element, such as, for example, a gas pressure tank like an oxygen tank. According to the invention, the carrying system consisting of the carrying device and the gas exchange device, without an external gas supply, is suitable for lung support only with a pump-operated ambient air suction section.

Advantageously, the gas exchange device has a housing that has a rear wall, facing the first carrying strap, which is curved inward toward the first carrying strap, whereby the housing can be kept close to the carrying strap so that the center of gravity of the gas exchange device, when used, comes to lie close to a patient's body, which increases wearing comfort and minimizes load on the patient due to a slight leverage.

In a advantageous embodiment, the curvature of the rear wall essentially corresponds to the curvature of the first carrying strap so that the rear wall of the housing abuts essentially flushly against the first carrying strap that is curved radially to the outside, which further optimizes wearing comfort.

It is, moreover, advantageous for the housing to have an average width, an average height running perpendicular to this width, and an average depth running perpendicular to the width and height, wherein the depth extends away from the rear wall, and wherein the maximum size of the depth is 20%—preferably, 15%—of the total overall length consisting of the width+height+depth. Due to this measure, the gas exchange device is provided with a flat design that, in a state of use, exerts only a slight leverage on the patient, so that the gas exchange device can be worn over a long time without fatiguing the patient.

Moreover, the device according to the invention or the system according to the invention can of course be designed so that they satisfy the general medical device directive, 93/42/EEC, or similar specifications.

BRIEF DESCRIPTION OF THE DRAWINGS

The invention, as well as advantageous embodiments thereof, will be explained below with reference to certain exemplary embodiments represented in the attached drawings, in which equivalent features are given the same reference numbers. The following is shown.

DETAILED DESCRIPTION OF THE INVENTION

Figure 1:
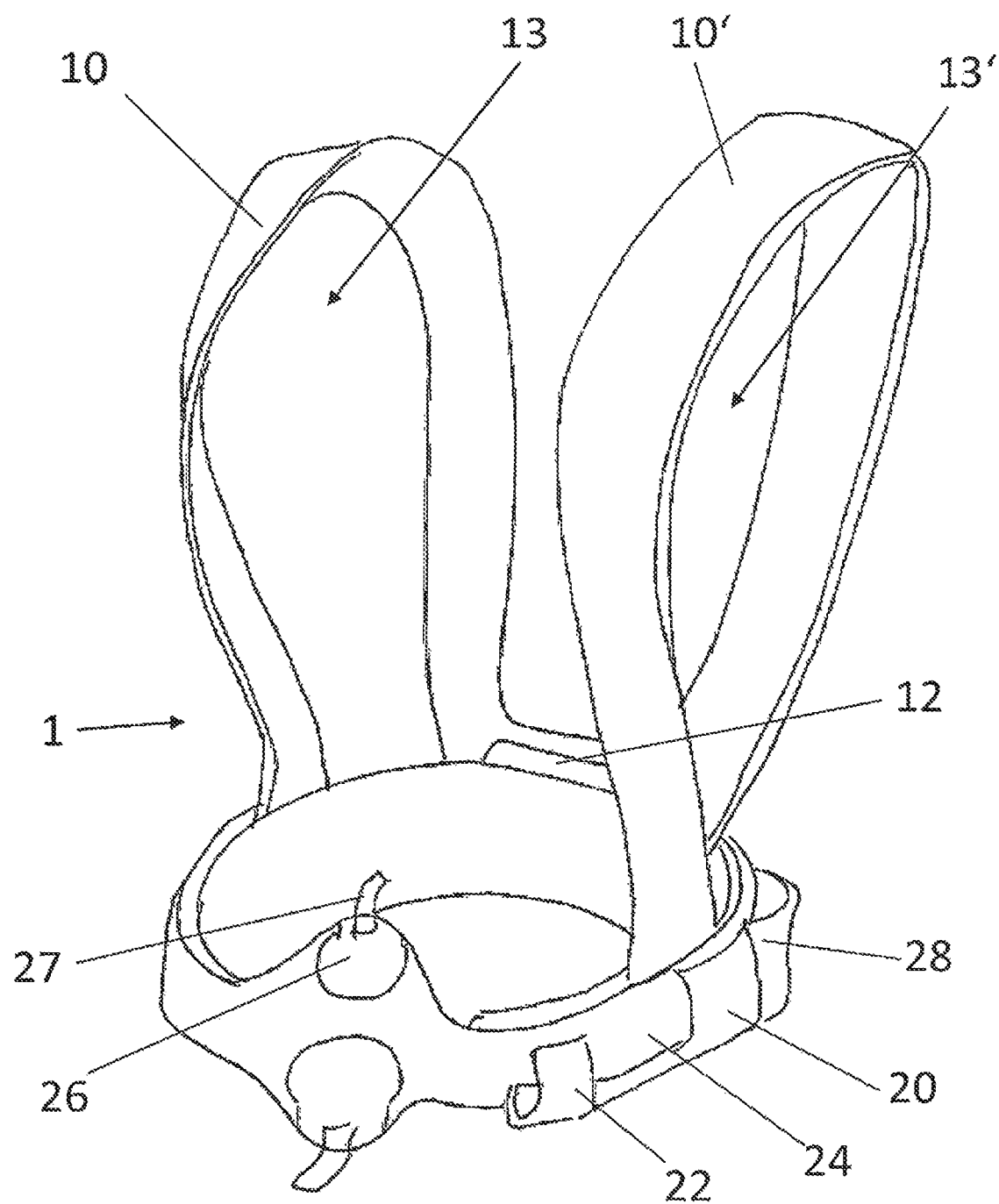
FIG. 1 shows a front view of a carrying device according to an embodiment of the present invention.

FIG. 1 shows a perspective front view of a carrying device 1 according to an embodiment of the present invention.

Here and in the following, to simplify the description of the present invention, an indicated direction is supposed to correspond to how it would be used when a patient properly wears the carrying device 1. "Top" accordingly designates a section that faces or is close to a head or shoulder of a patient. Correspondingly, a designation, "bottom," is used for sections or components of the carrying device 1 that are arranged or provided in a region of the carrying device 1 facing the feet of a patient. A direction from bottom to top, or vice versa, is designated a vertical direction. A direction perpendicular to the vertical direction, which, in particular, describes a circumferential direction around a torso, or a hip or waist of a patient is also designated a horizontal direction or alignment. A "front" position analogously describes a position that describes a front side of a carrier of the carrying device 1. A "rear" position correspondingly describes a side that would correspond to a back side, or a side of the back, of the carrier of the carrying device 1.

The carrying device 1 according to FIG. 1 has a first carrying strap 20 corresponding to the above definitions. The first carrying strap 20 runs in a horizontal direction and is intended to go around a torso or hip of a patient. The first carrying strap 20 therefore essentially forms a ring that runs from a front side around a lateral section across a rear side and a second lateral section of a patient's back to the front side.

Another carrying strapped 10 and a third carrying strap 10' each have a first leg 11a and a second leg 11b. The second carrying strap 10 and the third carrying strap 10' or the corresponding legs 11a and 11b run in a essentially vertical course. The legs 11a and 11b are designed as a single part in the embodiment shown in FIG. 1, so that the carrying straps 10, 10' transition into each other at a top section, and each form a loop. At least one of the legs 11a is fastened to an end of the first carrying strap 20. From the fastening point on the first strap 20, the leg 11a extends in a vertical direction and transitions into the second leg 11b at a topmost section. The second leg 11b of the carrying strap 10 can also be fastened to the first carrying strap 20. In other embodiments of the present invention, a bottom end of the second leg 11b of the second carrying strap 10 is connected to a bottom end of a leg of the third carrying strap 10'. The connection is made by means of a connecting bridge. A fastening means 12 is provided on the connecting bridge.

In the exemplary embodiment shown in FIG. 1, the fastening means 12 is a hook-and-loop (Velcro®) fastener. A corresponding mating part of the fastening means 12 is, according to FIG. 1, provided on the second carrying strap 20 so that the fastening means 12 can be securely fastened to the second carrying strap 20. In this manner, the second leg of 11b of the first carrying strap 10 or the third carrying strap 10' is fastened to the first carrying strap 20.

The fastening means 12 of the second carrying strap 10 or the third carrying strap 10' has a corresponding mating part of the fastening means 12 that interacts with the fastening means 12. The mating part of the fastening means is designed on the back section of the first carrying strap so that a connection can be made between the first carrying strap 20 and the second carrying strap 10 and the third carrying strap 10'.

According to the embodiment shown in FIG. 1, the second carrying strap 10 and the third carrying strap 10' accordingly have, in principle, a U-shape with a downward-facing opening that is bordered by the first carrying strap 20 when in a closed state, i.e., a state in which the carrying device is worn correctly. The loops formed by the carrying straps 10, 10' each constitute an opening 13, 13', through each of which a patient's arm can reach.

The first leg 11a of the second carrying strap 10 or 10' is fastened, in the shown embodiment according to FIG. 1, to a lateral, front section of the first carrying strap 20. The corresponding second leg 11b of the second carrying strap 10 or 10' runs to a rearward section, i.e., a rear region of a patient, when in a state of being worn.

Figure 2:
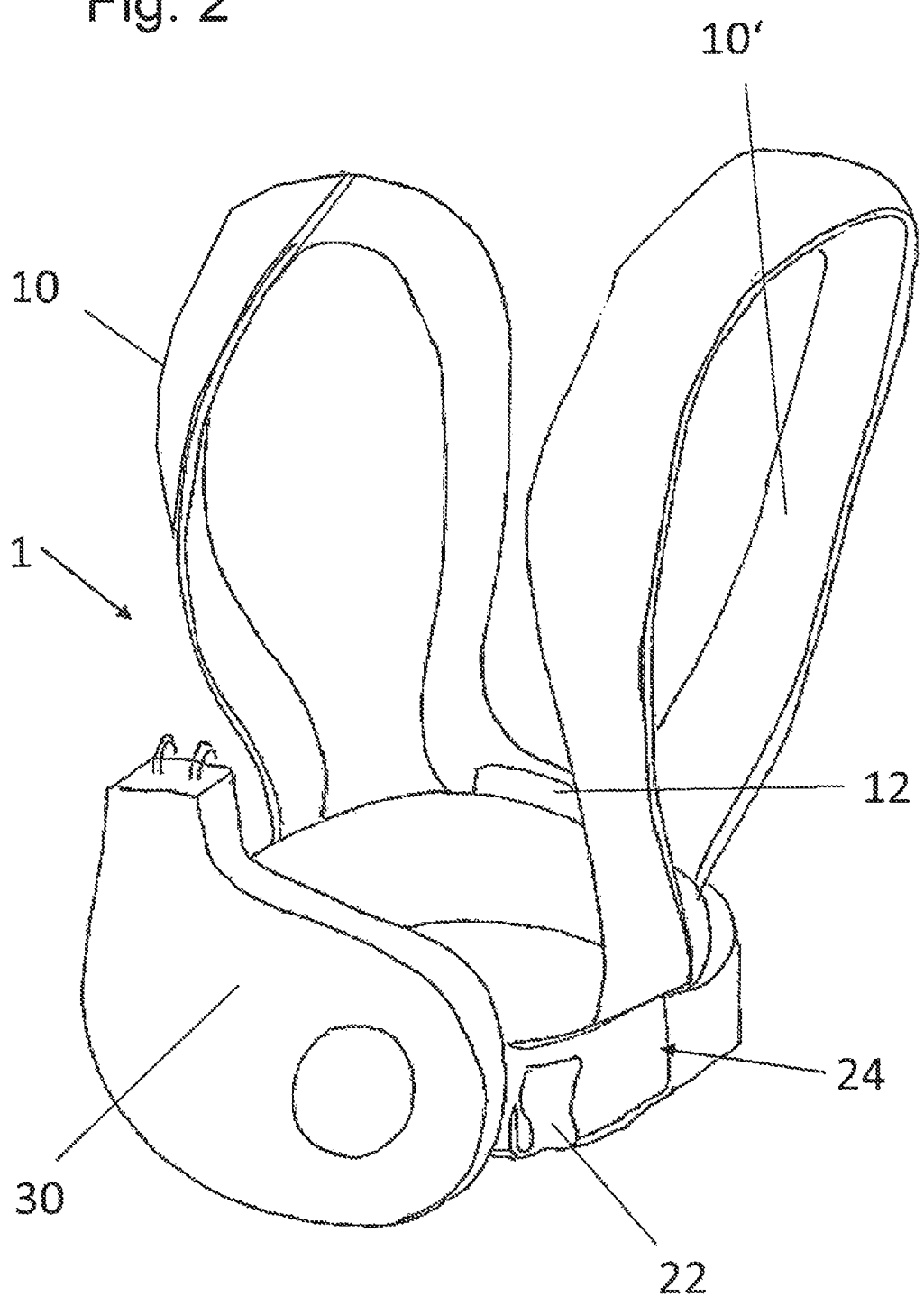
FIG. 2 shows the carrying device according to FIG. 1, with a portable gas exchange device.

The first carrying strap 20 moreover has a second closing means 24. The second closing means 24 can be designed in a manner similar to a Velcro fastener, like the fastening means 12. The second closing means 24 is configured in a circumferential direction of the first carrying strap 20. Accordingly, the second closing means 24 enables the first carrying strap 20 to be placed around the body of a patient, and the length of the first carrying strap 20 to be adapted. The second closing means 24 in the shown embodiment according to FIG. 1 is, moreover, partially configured as part of a fastening means 26. The fastening means 26 serves to hold a portable gas exchange device 30, as shown in FIG. 2. The fastening means 26 in the embodiment according to FIG. 1 has a holder for holding a projection or interlocking means fastened to the gas exchange device 30.

When the interlocking means of the gas exchange device 30 is inserted into the holder of the fastening means 26, an interlocking mechanism that, for example, is designed under spring pre-load in the holder of the fastening means 26 can be displaced so that the interlocking means of the gas exchange device 30 can penetrate deeper into the holder of the fastening means 26. By providing a notch or barb on the interlocking means of the gas exchange device 30, the engaging means can engage in the holder in the notch when the interlocking means is correspondingly inserted into the holder of the fastening means 26, and can accordingly secure the interlocking means of the gas exchange device 30 due to the engaging means, which engages under spring pre-load, on the carrying device 1. A releasing means—in this case, a flap 27—connected to the engaging means can also be formed on the fastening means 26 and causes the engagement of the engaging means with the projection of the gas exchange device 30 to be released. The releasing means can also be designed differently than by means of a flap.

In the embodiment in FIG. 1, the fastening means 26 of the carrying device 1 has two such holders offset in a vertical direction. This can bring about an improved grip, or reduce a tipping or slipping of the portable gas exchange device 30. The flaps 27 for releasing the engaging means in the fastening means 26 are configured in opposite directions—upwards for the top holder, and downwards for the bottom holder. This can enable easier access when removing the gas exchange device 30 from the carrying device. The holders can also be arranged offset, horizontally or in another manner, relative to each other.

A cable holder 22 is also formed on the first carrying strap 20. The fastening means 26 is formed on a front region, i.e., corresponding to a front side of a patient. The cable holder 22 is formed offset in a lateral direction adjacent to the fastening means 26.

The cable holder 22 can, for example, be designed as a flexible or ductile element that is self-closing due to an inherent spring pre-load, i.e., to lie with one leg on the carrying strap 20, similarly to a clamp. In a cross-sectional shape, the cable holder 22 is designed in the shape of a drop, i.e., formed to enclose a void. This void formed by the cable holder 22 is dimensioned so that at least one cable of a predetermined thickness can be held therein.

Moreover, according to the embodiment portrayed in FIG. 1, the first carrying strap 20 has a loop 28 in a lateral, rear section of the carrying strap 20. The loop 28 can, in particular, be formed by a fabric section fastened to the carrying strap 20. The loop 28 is dimensioned so that a holder is formed—for example, of a clamp section, i.e., a flat strip. In particular, as can be seen in FIG. 3, the loop 28 can serve to hold a retaining clip of a control unit 34.

FIG. 2 shows the carrying device 1 according to FIG. 1, wherein a portable gas exchange device 30 is arranged on a front side of the carrying device 1, i.e., on a front side of the first carrying strap 20. Of course, the portable gas exchange device 30 is fastened by at least one fastening means mating part to the fastening means 26 of the carrying device 1. The fastening means mating part is, in particular, a projection or an interlocking means. Preferably, the gas exchange device 30 has two corresponding interlocking means, corresponding to the fastening means 26 of the carrying device 1, for inserting into the holders of the fastening means 26.

Here and in the following, a consistent designation of the same or equivalently functioning components is used in the figures, and their description will not be repeated.

Figure 3:
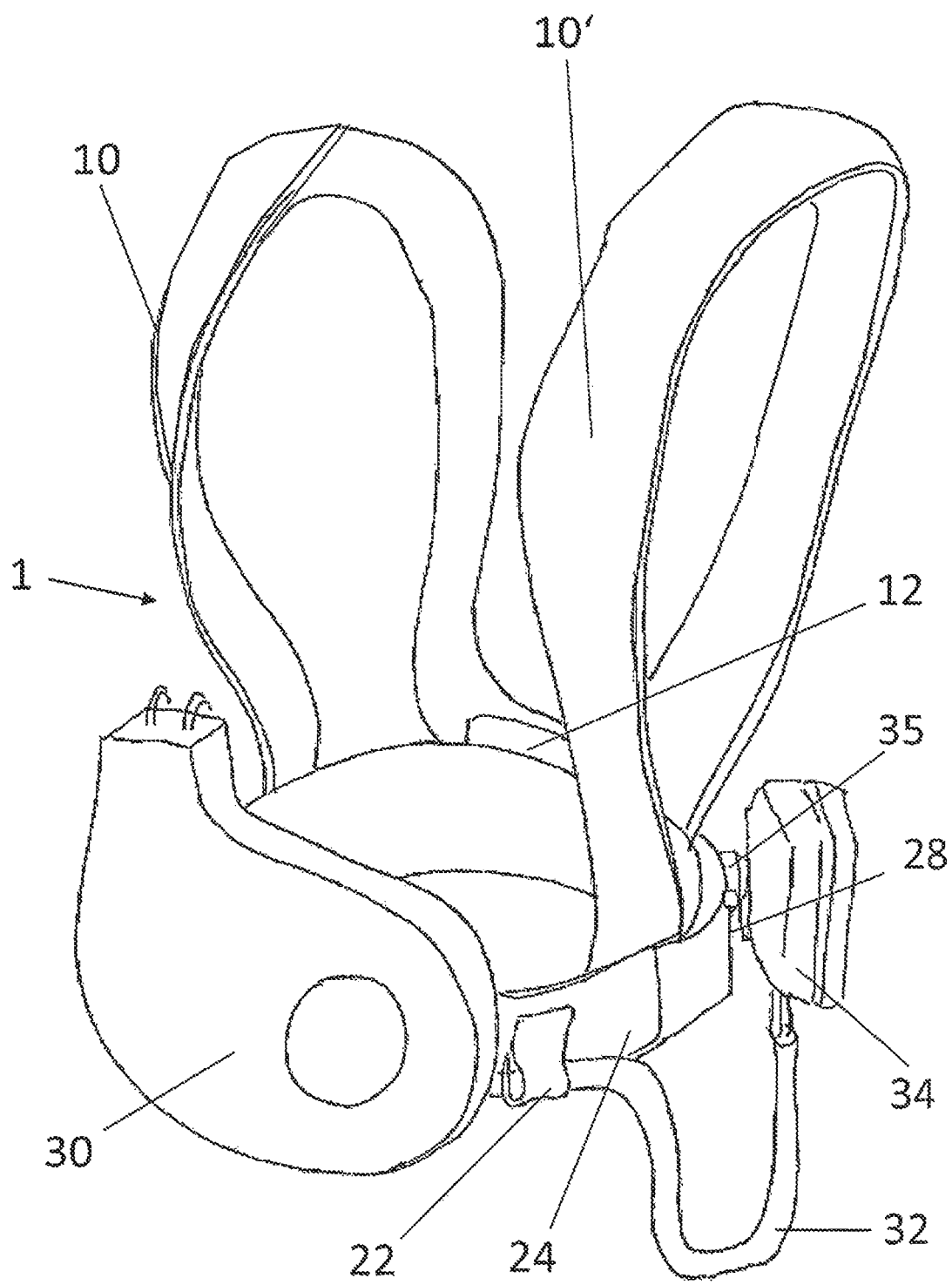
FIG. 3 shows the carrying device according to FIGS. 1 and 2, with a control unit.

FIG. 3 shows a carrying device 1 according to FIGS. 1 and 2, wherein, in addition to the portable gas exchange device, a control device 34 for controlling the portable gas exchange device 30 is portrayed. The control unit 34 has a fastening section 35. The fastening section 35 has a flat strip—in particular, a metal strip—that is intended to be held in the loop 28 of the second carrying strap 20. The width of the flat section of the carrying strap 35 and the width or dimensioning of the loop 28 are harmonized with each other, so that the control unit 34 can be securely held in the loop 28. The alignment of the loop 28 can thereby be provided in a vertical direction, as shown. Alternatively, the alignment of the loop 28 and, correspondingly, the alignment of the holding section 35 of the control unit 34 can be provided in a horizontal direction, i.e., in a circumferential direction.

Moreover, FIG. 3 shows a connection between the portable gas exchange device 30 and the control unit 34 by means of a cable 32. The cable 32 leads out of the portable gas exchange device 30 through the cable holder 22 and then runs further to the control unit 34. By providing the cable holder of 22, the cable 32 can run securely along the first carrying strap 20. In particular, the cable holder 22 can be dimensioned so that the cable 32 is clamped in the cable holder 22. It can thereby be possible for the cable 32 or the cable connections in the portable gas exchange device 30 to not be released from the gas exchange device 30 or control unit 34 due to unintentional pulling.

Figure 4:
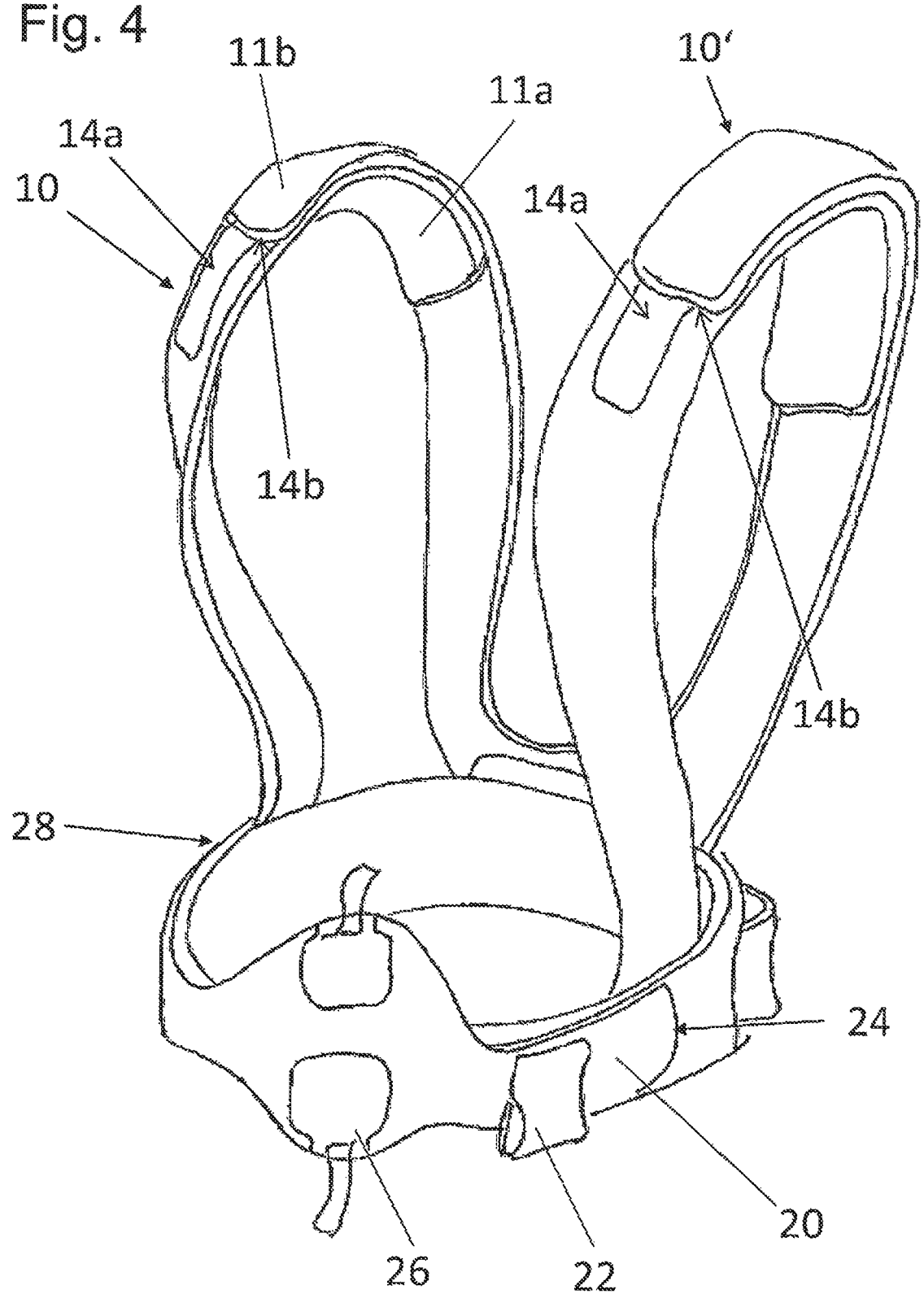
FIG. 4 shows a carrying device according to a further embodiment of the present invention.

FIG. 4 shows a further embodiment of a carrying device 1 according to the present invention. The embodiment in FIG. 4 differs from the embodiment in FIG. 1 in that two carrying straps separated from each other, viz., the second carrying strap 10 and third carrying strap 10', are provided. The carrying straps 10 and 10' are fastened to the first carrying strap 20 with the first leg 11a in each case, similarly to the embodiment according to the FIG. 1. The second leg 11b of the carrying straps 10, 10' is, however, fastened to the first leg of 11a of the respective carrying strap, so that the carrying straps each have a ring shape or O shape. In this case, an adjusting means 14a, 14b is provided on the carrying straps. The adjusting means 14a, 14b serve to change the length of the respective carrying strap and thereby make it possible to adapt the carrying device 1 to the physiology of a wearer.

In the shown embodiment of the first leg 11a of the carrying strap—described here with the second carrying strap 10 as an example—a first adjusting or locking means 14a is provided on an open end section of the leg 11a. The adjusting and locking means 14a in the shown embodiment is, for its part, designed as a part of a Velcro fastener that is formed to be flat along the end section of the first leg 11a of the second carrying strap 10. On a free end section of an open end of the second leg 11b, an adjusting or locking means 14b is provided that is complementary to the first locking means 14a and, for its part, is formed to be flat along the end section 11b, and forms a second part of the Velcro fastener. In this manner, a secure, flat connection between the legs 11a and 11b of the second carrying strap 10 is enabled. Analogously, such a closing means is also formed on the third carrying strap 10'.

In the embodiment according to FIG. 4, the closing means 24 is, moreover, provided in a rear region of the first carrying strap 20. Moreover, the position of the loop 28 in the embodiment according to FIG. 4 is modified such that the loop 28 is formed in a lateral/front region of the first carrying strap 20.

Of course, the position of the closing means, the loop, or other components is freely selectable and does not restrict the inventive concept of providing a carrying device for a portable gas exchange device or a carrying system according to the invention.

Figure 5:
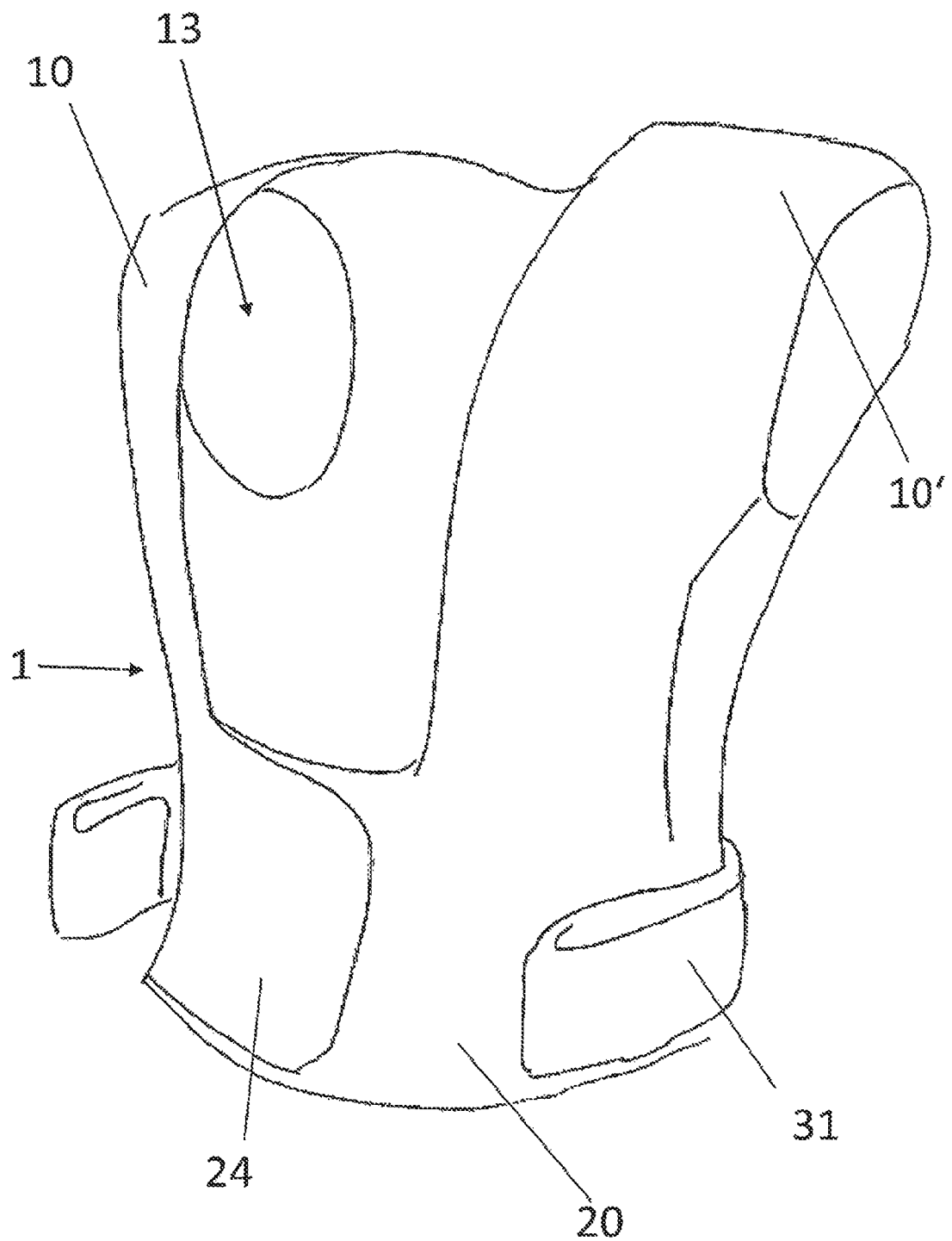
FIG. 5 shows a carrying device according to a further embodiment of the present invention.
Figure 6:
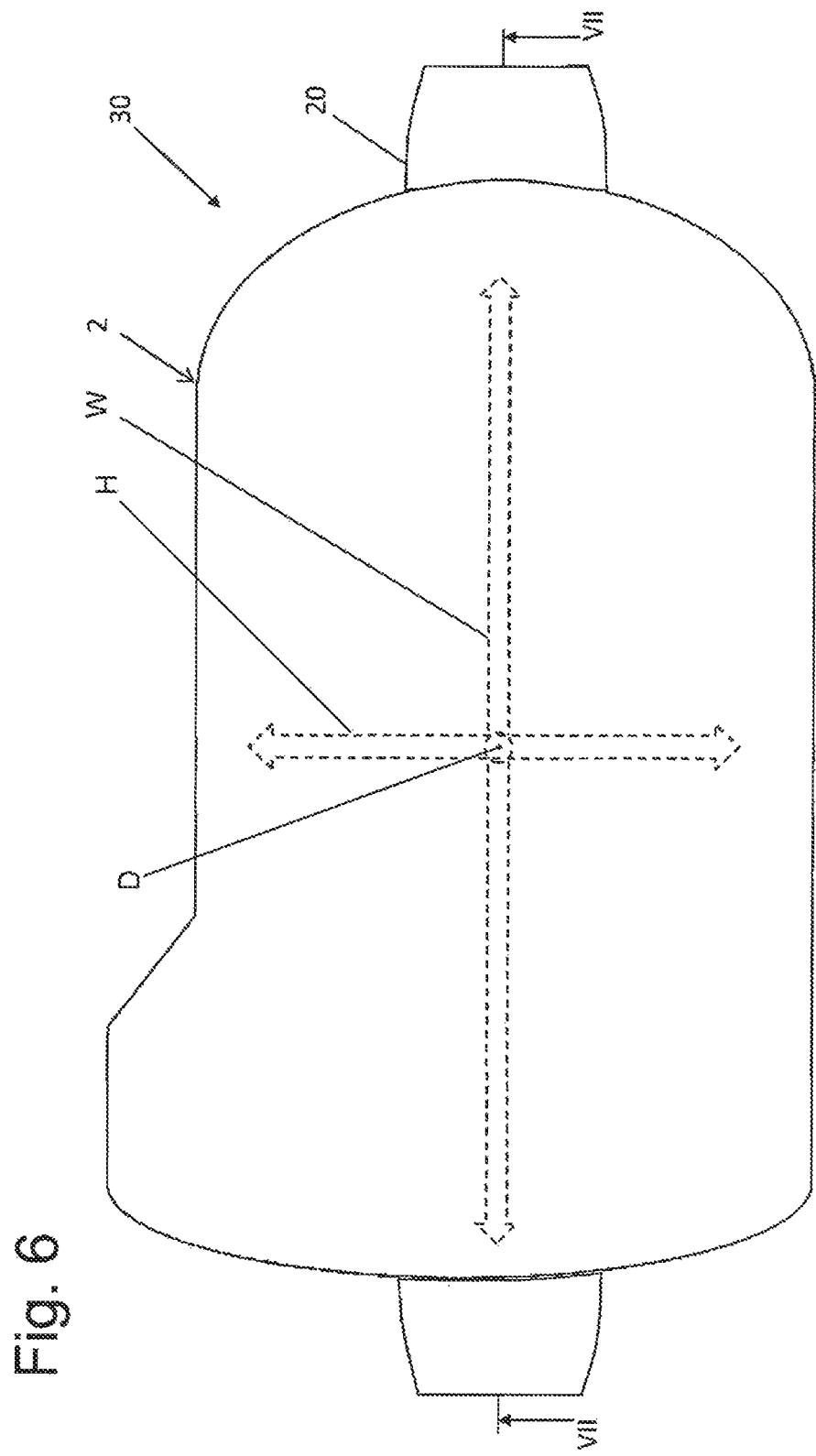
FIG. 6 shows a carrying system containing only one indicated carrying device and a gas exchange device of which only a housing is depicted.

Accordingly, FIG. 5 shows a further embodiment of the present invention, wherein the first carrying strap 20, the second carrying strap 10, and the third carrying strap 10' are designed together as a single part. The carrying device 1 in this context is designed so that it can be worn similarly to a patient's vest. The carrying device 1 is designed so that a flat hold—in particular, in a shoulder region and a back region, as well as in a stomach region, of a patient—is enabled. The closing means 24 in the embodiment according to FIG. 6 is provided in a front region of the carrying device 1. In addition, the embodiment according to FIG. 5 has an additional belt means 31 that can also go around the torso, hips, or waist of a wearer and is provided for fastening the portable gas exchange device 30. The belt 31 can also be designed to hold the control unit 34 and/or the cable 32. The gas exchange device 30 in this embodiment can, on the other hand, be fastened with a fastening means 26 (not shown in FIG. 5) to the carrying device 1, wherein the fastening means can be held by means of the belt 31, or fastened to the belt 31.

Preferably, although not discernible in FIG. 5, the carrying device 1 according to an embodiment in FIG. 5 has a first part of a preferably flat fastening means such as a Velcro fastener in a region in which belt 31 goes around the carrying device 1 or a carrier. Analogously, the belt 31 can have a corresponding complementary part of the fastening means. This can enable a secure—preferably, flat—connection between the belt 31 and the carrying device. Instead of a fastening means, a friction means, such as rubberization or the like, can be provided which prevents the belt 31, when worn, from slipping along the carrying device 1. Closing the belt 31 can thus easily prevent or limit slippage of the gas exchange device 31 which can be fastened to the belt 31, and the load from the gas exchange device can be held by the shoulders of a patient and distributed over the entire body.

Figure 7:
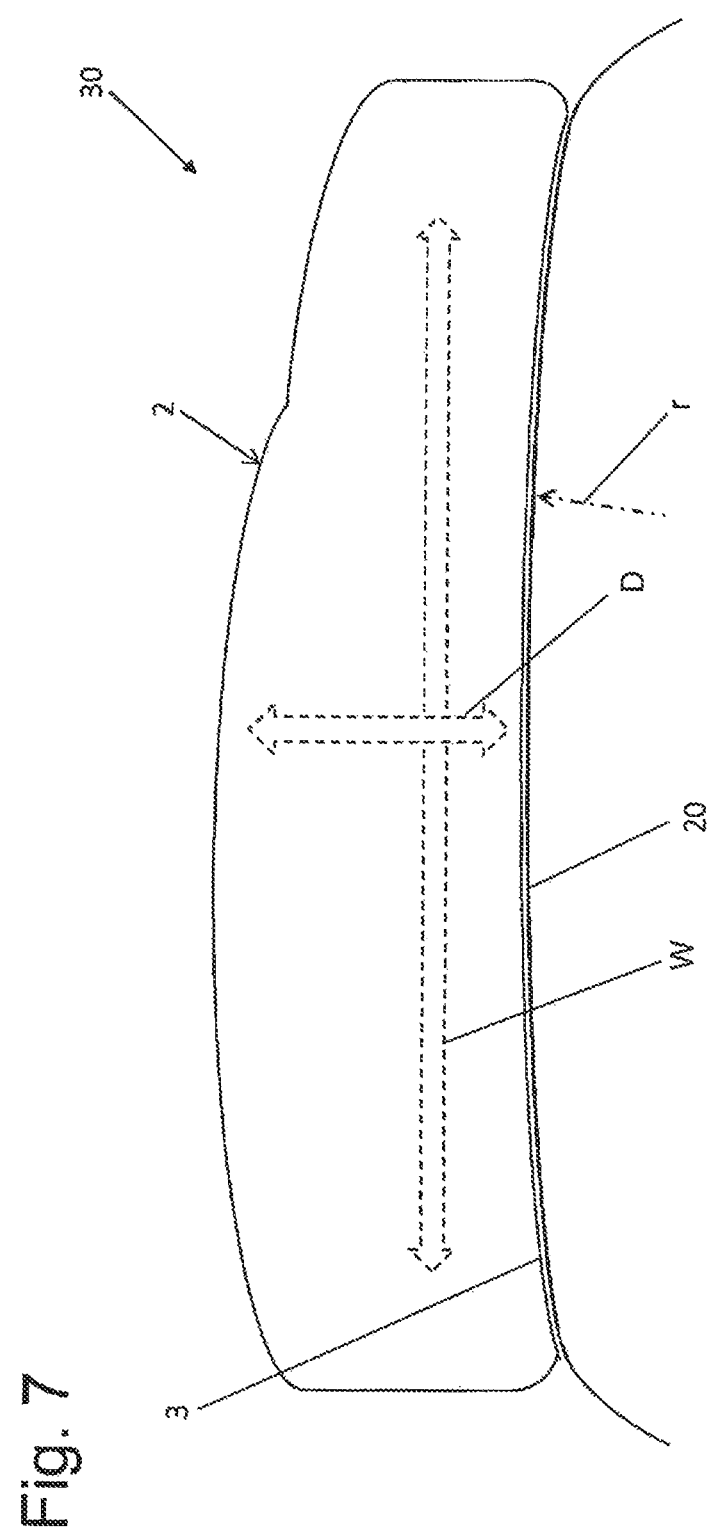
FIG. 7 shows a housing of the gas exchange device and a carrying strap of the carrying device of the carrying system from FIG. 6 in a section along line VII-VII from FIG. 6.

A housing 2 of the gas exchange device 30 and the first carrying strap 20 of the carrying device 1 of the carrying system is depicted in FIGS. 6 and 7. The carrying system represents a portable medical gas exchange system that combines the above-described carrying device 1 and the likewise above-described gas exchange device 30 with each other.

As can be seen in FIGS. 6 and 7, the housing 2 extends to an average width W, an average height H running perpendicular to said width W, and an average depth D running perpendicular to the width W and height H. In the present case, reference is made to the average width, height, and depth, since the housing 2 has an "organic" form with rounded sides and is substantially free of corners. The depth D extends thereby out from a rear wall 3 of the housing 2. The depth D has a maximum size of 20%—preferably, 15%—of the total overall length, or the total of the width W+height H+depth D. This lends the gas exchange device a flat design that, in a state of use, exerts only a slight leverage on the patient, so that the gas exchange device can be worn over a long time without fatiguing the patient.

As can be seen, in particular, from FIG. 7, the rear wall 3, facing the first carrying strap 20, of the housing 2 is curved inward (concave) toward the first carrying strap 20, whereas the first carrying strap 20, at least when the closing means 24 is in a closed state, curves radially outward (convex), wherein the radius of curvature r differs by section, as can be seen, in particular, from FIGS. 1 through 5.

The curvature of the rear wall 3 essentially corresponds to the curvature of the first carrying strap 20, so that the rear wall 3 of the housing 2 abuts essentially flushly against the first carrying strap 20 curved radially outward, which causes the gas exchange device 30 of the carrying system or the portable medical gas exchange to lie close to a patient's body, which increases wearing comfort and minimizes the load on the patient, due to restricted leverage.

Figure 8:
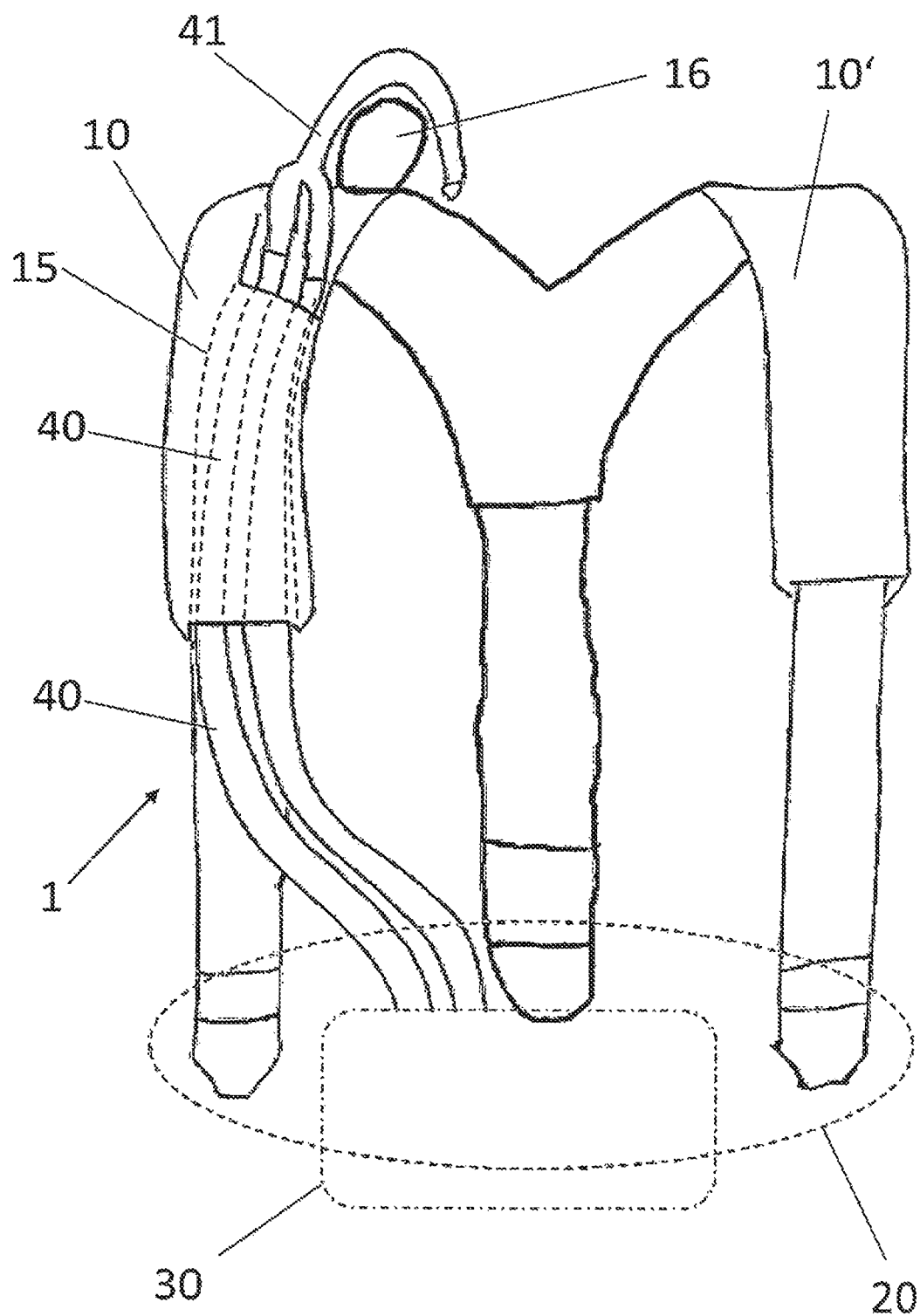
FIG. 8 shows a carrying device according to a further embodiment of the present invention.

FIG. 8 depicts a further embodiment of a carrying device 1 according to the invention, in which the first carrying strap 20 is depicted only in passing, just as with the gas exchange device 30. The embodiment portrayed in FIG. 8 of a carrying device 1 for a gas exchange device 30 differs from the embodiment portrayed in FIG. 1, in particular, in that, on a second carrying strap 10, that optionally can be a left or right carrying strap 10, a carrying tunnel 15 for hoses 40—in particular, blood-carrying hoses 40—which run from and to the gas exchanger 30, can be connected to the blood circulatory system of a patient by a double cannula 41 in the event that the carrying device 1 and the gas exchange device 30 are used. In the shoulder region of the carrying strap 10 that has the carrying tunnel 15, a support or guide element 16 is also provided through which a section of the double cannula 41 is guided in order to come to lie in a defined position relative to a patient. In the present embodiment, the two carrying straps 10, 10' are connected to each other in a rearward section, so that a Y-shaped geometry results.

Figure 9:
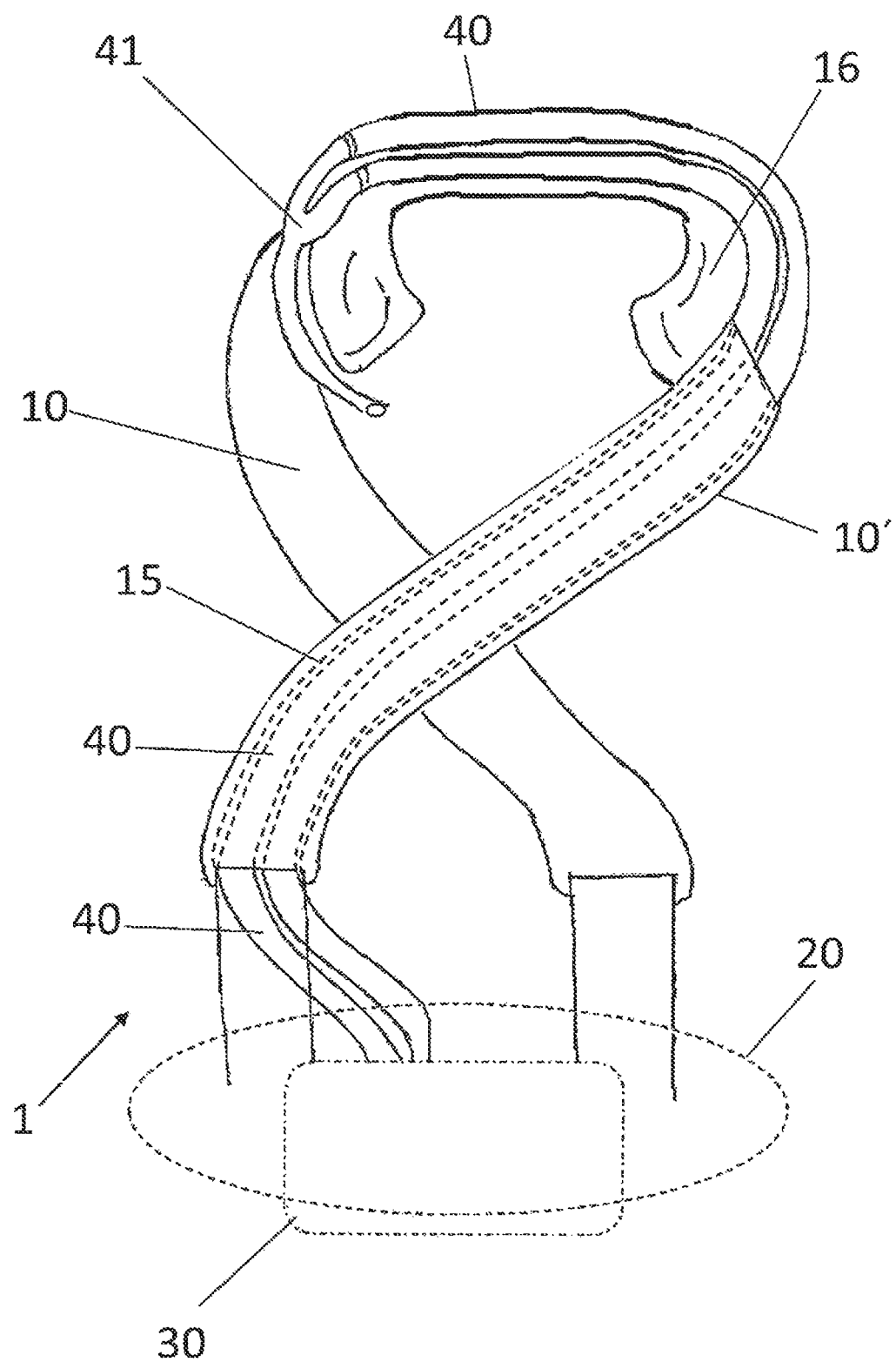
FIG. 9 shows a carrying device according to a further embodiment of the present invention.

FIG. 9 portrays a further alternative embodiment of a carrying device 1 according to the invention that differs from the previous one in that the carrying device 1 does not have a rearward section, and that the two carrying straps 10, 10' are connected to each other behind a collar section 16 of the carrying device 1, where they go around the collar section 16 in a loop. In one of the carrying straps 10', there is also a carrying tunnel 15 for conducting—in particular, blood-carrying—hoses 40 from the gas exchange device 30 to the patient. The blood-carrying hoses 40 in turn terminate at the collar section 16 in a double cannula 41 that is led on the collar section 16 such that it is again positioned for optimal access to the blood circulatory system of a patient who is wearing the carrying device and the gas exchange device.

Of course, in addition to the exemplary embodiments presented here, other alternative embodiments are conceivable in the context of the present invention. Of course, the present invention is equally applicable to a variety of materials, such as natural or synthetic fabrics, elastic or non-elastic fabrics, breathable, tear-resistant, water-repellent, sterile or sterilizable, and other fabrics. Moreover, the fabrics can be woven, sewn, and melted to each other, or be otherwise connectable to each other.

In addition, the carrying device—in particular, at places where intensive contact with a patient's body predominates, such as the shoulders or the hips of a patient—padding or additional materials or means can be provided, without departing from the subject matter of the invention.

In some embodiments, in which the gas exchange device has an ambient air suction section, the suction of the ambient air can be directly done at the gas exchange device. Alternatively, the ambient air suction section can have a suction hose that is conducted along the carrying device, e.g., like a hose of the extracorporeal blood circulatory system, or a cable of the control unit, and can suck air in at a predetermined location of the carrying device. In particular, air in the head region of a patient can be sucked in, where there may be fewer airborne particles in the air. Moreover, covering the ambient air suction section, e.g., by clothing in front of the gas exchange device, and an associated reduction in the suppliable air can, in this way, be avoided.

The invention claimed is:
1. A body-worn blood-gas exchange system, comprising:
a portable gas exchange device comprising;
   a housing;
   a pump system disposed in the housing;
   a gas exchange element disposed in the housing and interconnected with the pump system;
   the gas exchange device operable to draw in ambient air and blood from a patient and to exchange gas between the ambient air and the blood for patient support;
   the gas exchange device further having a fastener on the housing;
a carrying device for carrying the gas exchange device on the patient's body, the carrying device comprising;
   a first carrying strap adapted to go around the patient's torso, the first carrying strap having a front region to be positioned on a front side of the torso, an opposed rear portion to be positioned on a rear side of the torso, and two side portions extending between the front and rear portions, the first carrying strap having a outwardly curved outer face in at least the front region
   a fastener disposed on the outwardly curved face of the front region of the first carrying strap, the fastener on the housing of the gas exchange device being complementary to the fastener of the carrying device, such that the portable gas exchange device is fastened to the front side of the carrying device;
   a second carrying strap adapted to go over a first shoulder of the patient, the second carrying strap being fastened to one of the side portions of the first carrying strap and is spaced from a side of the portable gas exchange device, the second carrying strap configured to transfer a weight of the carrying device and components attached thereto;
   a third carrying strap that is symmetrical to the second carrying strap and is configured to go around a second shoulder of the patient, the third carrying strap being fastened to the other of the side portions of the first carrying strap and is spaced from an opposing side of the portable gas exchange device;
a blood carrying hose; and a double cannula connected to the blood carrying hose and configured to be connectable to the patient's blood circulatory system;

wherein the gas exchange system is fastened to the carrying device by the fastener on the housing engaging the at least one fastener of the carrying device and the blood carrying hose runs to and from the portable gas exchange device and is connectable to the patient's blood circulatory system via the double cannula;

wherein the body-worn blood-gas exchange system requires no external gas tank, thereby allowing the body-worn blood-gas exchange system to be carried entirely on the patient's body for highly mobile use.

2. A carrying system according to claim 1, wherein the fastener of the portable gas exchange device and/or the at least one fastener of the carrying device is a hook-and-loop fastener.

3. A carrying system according to claim 1, wherein the second carrying strap is fastened to the first carrying strap by a hook-and-loop fastener and the third carrying strap is fastened to the first carrying strap by a hook-and-loop fastener.

4. The body-worn blood-gas exchange system according to claim 1, wherein:
the first carrying strap further has an additional fastener on the rear portion and a cable holder on one of the side portions between the fastener on the front portion and the additional fastener on the rear portion;
the portable gas exchange device further comprises a control unit, the control unit having a fastener adapted to fasten to the additional fastener on the rear portion of the first carrying strap; and
the portable gas exchange device further having a cable connecting the control unit to the housing;
wherein the cable is held by the cable holder on the side portion of the first carrying strap.

5. The body-worn blood-gas exchange system according to claim 4, wherein:
the cable holder runs within the side portion of the first carrying strap; or
the cable holder is a self-closing holder that closes under spring force.

6. The body-worn blood-gas exchange system according to claim 1, wherein:
the housing of the portable gas exchange device has a rear wall facing the first carrying strap, the rear wall curving inwardly so as to be complimentary to the outwardly curved outward face of the front portion of the first carrying strap, such that the rear wall of the housing essentially abuts flushly against the front portion of the first carrying strap which is curved radially to the outside, the fastener on the housing being defined on the inwardly curving rear wall of the housing.

7. The body-worn blood-gas exchange system according to claim 6, wherein the housing has an average width (W), an average height (H) running perpendicular to this width (W), and an average depth (D) running perpendicular to the width (W) and height (H), wherein the depth (D) extends away from the rear wall, and wherein the maximum size of the depth is 20% of the sum of the width (W)+height (H)+depth (D).

8. The body-worn blood-gas exchange system according to claim 1, wherein:

the second carrying strap guides the blood carrying hose and/or double cannula over the shoulder of the patent; and
the double cannula has a bend so as to be connectable to the patient's blood circulatory system in a shoulder region.

9. The body-worn blood-gas exchange system according to claim 8, further comprising:
a collar section connected between the second carrying strap and the third carrying strap;
the collar section guiding the blood carrying hose and/or double cannula so as to be connectable to the patient's blood circulatory system in a shoulder region.

10. The body-worn blood-gas exchange system according to claim 8, further comprising a hose holder on the second carrying strap, the hose holder being positioned such that the double cannula is guided therethrough to come to lie in a defined position relative to the patient's shoulder region.

11. The body-worn blood-gas exchange system according to claim 10, wherein the hose holder is defined on an inside of the second carrying strap, facing the patient's torso, so as to reduce heat loss.

12. The body-worn blood-gas exchange system according to claim 1, wherein the portable gas exchange device further comprises a control unit, the control unit being:
at least partially integrated into the carrying device; and/or
the portable gas exchange device and/or the control unit has a transmitting and/or receiving unit for wirelessly connecting the portable gas exchange device to the control unit.

13. The body-worn blood-gas exchange system according to claim 1, further comprising an alarm button and/or a mobile communications device.

14. The body-worn blood-gas exchange system according to claim 1, wherein the portable gas exchange device has an ambient air suction section, the ambient air suction section comprising:
a filter for filtering ambient air; and/or
a suction hose extending along the carrying device for intake of ambient air spaced from the housing.

15. The body-worn blood-gas exchange system according to claim 1, wherein the fastener on the first carrying strap comprises two holders offset from each other.

16. The body-worn blood-gas exchange system according to claim 15, further comprising a flap associated with each holder for releasing the respective holder from the fastener on the housing.

17. The body-worn blood-gas exchange system according to claim 1, wherein first, second and third carrying straps are interconnected as a single part.

18. The body-worn blood-gas exchange system according to claim 1, wherein carrying device further comprises:
at least one closure for opening and closing at least one of the carrying straps; and/or
at least one adjustor for adapting a length of at least one of the carrying straps.

19. The body-worn blood-gas exchange system according to claim 1, wherein the portable gas exchange device is operable to perform decarboxylation of the patient's blood using ambient air.

* * * * *

UNITED STATES PATENT AND TRADEMARK OFFICE
CERTIFICATE OF CORRECTION

PATENT NO. : 11,044,984 B2  
APPLICATION NO. : 15/738943  
DATED : June 29, 2021  
INVENTOR(S) : Georg Matheis et al.

Page 1 of 1

It is certified that error appears in the above-identified patent and that said Letters Patent is hereby corrected as shown below:

In the Claims

Column 15, Line 14, Claim 2 delete "A carrying" and insert --The body-worn blood-gas exchange--

Column 15, Line 18, Claim 3 delete "A carrying" and insert --The body-worn blood-gas exchange--

Column 16, Line 2, Claim 8 delete "patent" and insert --patient.--

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*